United States Patent [19]
Martin et al.

[11] Patent Number: 6,149,819
[45] Date of Patent: *Nov. 21, 2000

[54] AIR AND WATER PURIFICATION USING CONTINUOUS BREAKPOINT HALOGENATION AND PEROXYGENATION

[75] Inventors: Roy Martin, Downers Grove; Mikel Anthony Ferri, Bradley, both of Ill.

[73] Assignee: United States Filter Corporation, Palm Desert, Calif.

[*] Notice: This patent is subject to a terminal disclaimer.

[21] Appl. No.: 09/260,810

[22] Filed: Mar. 2, 1999

[51] Int. Cl.$^7$ ..................................................... C02F 1/76
[52] U.S. Cl. .................. 210/743; 210/746; 210/752; 210/754; 210/755; 210/756; 210/759; 210/764; 210/908; 210/916
[58] Field of Search ..................... 210/743, 746, 210/752, 754–756, 758, 759, 764, 908, 916

[56] References Cited

U.S. PATENT DOCUMENTS

| | | | |
|---|---|---|---|
| 3,702,298 | 11/1972 | Zsoldos et al. | 210/759 |
| 4,752,740 | 6/1988 | Steininger | 210/169 |
| 5,130,033 | 7/1992 | Thornhill | 210/754 |
| 5,306,432 | 4/1994 | Puetz | 210/759 |
| 5,332,511 | 7/1994 | Gay et al. | 210/755 |
| 5,683,654 | 11/1997 | Dallmier et al. | 422/14 |
| 5,814,233 | 9/1998 | Starkey et al. | 210/759 |
| 5,849,985 | 12/1998 | Tieckelmann et al. | 210/759 |
| 5,858,246 | 1/1999 | Rafter et al. | 210/754 |
| 5,882,526 | 3/1999 | Brown et al. | 210/753 |

*Primary Examiner*—Peter A. Hruskoci
*Attorney, Agent, or Firm*—Mchale & Slavin

[57] ABSTRACT

A process for optimizing the rate of oxidation using a combination of halogen, e.g. chlorine donors and peroxygen, e.g. potassium monopersulfate. The peroxygen compound elevates the oxidation-reduction potential of the body of water being treated. Simultaneously, a halogen donor is added to the body of water to maintain a PPM level of free halogen sufficient to insure sanitization. The feed rates and concentrations of both oxidizers are optimized so as to achieve and maintain the targeted parameters. A high level of oxidation is maintained which removes by-products from the water and surrounding air.

12 Claims, 2 Drawing Sheets

AIR AND WATER PURIFICATION USING CONTINUOUS BREAKPOINT HALOGENATION AND PEROXYGENATION

This invention is related to co-pending application Ser. No. 09/206,809, entitled "Air and Water Purification Using Continuous Breakpoint Halogenation" the contents of which are herein incorporated by reference.

FIELD OF THE INVENTION

This invention relates to the maintenance of aquatic facilities, and in particular, to the optimization of the feed rates of a sanitizer/oxidizer and peroxygen compound to eliminate the accumulation of undesirable halogenated compounds, thereby increasing water and air quality within such facilities.

BACKGROUND OF THE INVENTION

The use of closed recirculating water reservoirs for use by the general public, for example, swimming pools, spas, hot tubs, decorative fountains, cooling towers and the like, has led to a variety of water quality problems. For instance, improper chemical balances in the water can lead to various types of contamination including bacterial and viral contamination.

The use of chemical sanitizers is a fairly standard water sanitation method. Addition of so-called halogen donor compounds, such as chlorine or bromine are effective sanitizers so long as they are maintained at well defined and constantly controlled concentration levels in the water. It is important that the concentration of these chemical sanitizers is not allowed to become too high which may cause irritation to the users and damage to the water system. Insufficient sanitizers result in a contaminated condition.

The difficulties in maintaining a proper balance of sanitizers may arise from numerous load factors that are difficult, if not impossible, to predict. For instance, in a pool the load factor is typically caused by varying numbers of users. In hot tubs the use of air jets and high water temperatures tend to destroy or remove the sanitizer from the water. Cooling towers are subject to environmental conditions, such as fluctuations in temperature. Indoor decorative fountains may be affected by the air quality in the building, while the fountain water can also affect the air in the building.

Various testing devices exist for determining the chemical balance of the water of pools, spas and the like, for example, colormetric chemical test kits are available that utilize liquid droplets, test strips or tablets which dissolve in the water to indicate a particular level or concentration of sanitizing agents. By removing a test sample of water, for example via a scoop or cup, a seemingly representative sample is deemed to have been taken. A staining agent is then added by means such as an eye dropper or the like. The degree of staining relates to the amount of sanitizer in the water. The amount of sanitizer present is determined by visually comparing the degree of coloring of the test sample against a test scale previously formulated. Further complicating the task of maintaining sanitary conditions in such bodies of water is the fact that studies now indicate there is little correlation between the free halogen, e.g. chlorine, residual readings which are normally used to monitor such bodies of water and the actual bacteriological quality of the reservoirs themselves. Pool and spa maintenance officials have long gone under the assumption that maintaining a free chlorine residual of two milligrams per liter or two parts per million will insure a safe water condition. Thus, the parts per million reading which is determined via the stain comparison, is actually a reflection of the sum of the free chlorine and combined chlorine compounds such as chloramine which are present in the water. These combined chlorine derivatives do not protect from bacteria and/or viral contamination. Additionally, since organic and chemical loading drastically reduce the ability of free chlorine to overcome bacteria, the available free chlorine test kits are of questionable value unless the exact levels of organic contaminants and the particular pH of the water being tested is known.

U.S. Pat. No. 4,752,740 suggests the use of monitoring the oxidation-reduction potential (ORP) as a method of measuring the sanitization levels of water. ORP defines the potential of a sanitizer such as chlorine, bromine or ozone to react with various contaminants. These compounds are known as oxidizers and have the property of "burning off" impurities in the water, for example, body wastes, algae and bacteria. The use of an ORP sensor allows the pool maintenance engineer to measure the potential generated by the active form of the sanitizer and not the inactive forms such as the combined chlorine derivatives. Additionally, ORP monitoring has an advantage in that it is an ongoing electronic process requiring no test chemicals or agents and monitoring of sanitation levels is constantly performed as opposed to being performed on some predetermined schedule basis. Since the potential for disease transmission due to organic loading is far more significant in public spas and pools, use of ORP measurement could be of great benefit in reducing the risk of contamination and disease transmission.

In accordance with standards set forth by the World Health Organization in 1972, maintenance of an ORP level of 650 millivolts is deemed to result in a water supply that is disinfected and in which viral inactivation is virtually instantaneous.

Chlorine is the most widely used oxidizer in the aquatic industry, the primary use being for sanitation of the water in pools and spas. Chlorine, being an oxidizer, is also involved in oxidation reactions with various organics, as well as inorganic and organic nitrogen based substances such as urea, uric acid, amino acids, etc. One of the drawbacks of chlorine is the production of chlorinated byproducts resulting from incomplete oxidation. These byproducts are often volatile and produce undesirable side effects such as irritation of the eyes, sinuses, skin, foul smelling air, and corrosion of air handling equipment.

The health department generally regulate the concentration of Free (HOCL & OCL) chlorine in the water. In some locations, sufficient HOCL is not available to maintain a sufficient rate of oxidation of the demand being contributed to the water. This allows for the accumulation of these undesirable substances. Substances which oxidize following substoichiometric oxidation react with the chlorine producing substoichiometric and/or stoichiometric compounds. Further oxidation with HOCL eventually leads to increased concentration of substances that follow stoichiometric oxidation, such as monochloramines. If enough HOCL is not maintained to meet the stoichiometric ratios needed to drive oxidation of the chloramines, no demand on the HOCL is experienced. However, when the chlorine donor(s) are controlled using ORP control with an optimized ORP setting of between 780–800 mV, the buffering effect chloramines place on the ORP becomes a significant factor. The buffering effect provided by the chloramines reduces the impact on ORP provided by the addition of more chlorine donor(s). The controller feeds more chlorine donor(s) to achieve the optimized ORP. This often leads to levels of Free Chlorine which exceed local maximum limits. In order to meet the maximum limits of free chlorine, the ORP is reduced so as to not exceed the established limit. This allows for the volatile chlorinated compounds to accumulate, thereby increasing the partial pressure which promotes fouling of the air.

Numerous attempts have been made at addressing this problem. "Shocking" of the pool water requires dosing the water with stoichiometric concentrations of chlorine to oxidize the substances. One problem with this method is that there cannot be any bathers present due to the excessive concentrations of chlorine required to meet the stoichiometric levels needed when said undesirable substances have been allowed to accumulate. Another issue is this method is generally applied after the symptoms have appeared, i.e. high combined chlorine, foul odors, etc. In many cases this method fails to rid the water and air of these substances since the concentration of chlorine required is at best a rough estimate (incorporates measuring the combine chlorine in the water). Measuring the concentration of combined chlorine in the water does not take into consideration the accumulated demand that is non-aqueous, e.g. that accumulated on the filter media, walls of the pools, etc. As the chlorine levels rise, some of the accumulated demand is liberated. This gives the appearance that the system had not been driving breakpoint when indeed it probably did for awhile. The fact that the free chlorine levels drop considerably, and the combined chlorine level still appears, is an indication the HOCL must have oxidized the combined chlorine and/or accumulated demand, thereby providing a source of readily available oxidizable substances not originally detected in the water. When the free chlorine levels rise, they oxidize substances in the filters and the remaining system. This releases more substances into the water which were not accounted for, the stoichiometric ratio of HOCL is overtaken, and breakpoint is not achieved.

Ozone has been used as a side stream treatment to destroy these undesirable substances. While effective, ozone cannot be applied to the bulk water of the pool where the contaminants are being added. Also, since ozone cannot be used as a stand-alone treatment since it cannot maintain a residual in the water, chlorine or bromine is used as the primary sanitizer. Besides being expensive and often requiring extensive deozonation equipment, e.g. such as activated carbon, ozone destroys chlorine by attacking the hypochlorite ions, thereby further increasing operational and maintenance cost.

Bromine is sometimes used in place of chlorine because of the belief it does not produce the air fouling byproducts produced by chlorine. However, while bromamines are not as volatile as chloramines, they do possess an odor and irritate the eyes. Bromine also requires an oxidizer such as chlorine or ozone to activate the bromide ion. Operating costs tend to be high and it is often difficult to maintain water quality since no easy methods are available for differentiating between free or combined bromine. Also, hydantoin, an additive commonly used to pelletize the bromine chlorine combination, reduces the oxidizing power of the bromine as the hydantoin accumulates in the water. This makes it more difficult to reduce the accumulation of undesirable brominated compounds.

Non-chlorine shock treatments incorporating peroxygen compounds, e.g. potassium monopersulfate (MPS) have been sold under the brand name OXY-BRITE for addressing the chloramine issue. Despite the application of this product following manufacturer's guidelines, many pools continue to experience chronic air and water quality problems. The method of shock feeding is a means of addressing the symptoms resulting after the problem makes them apparent, e.g. high chlorine concentration and foul odors. MPS is approved for use as a shock treatment while bathers are present. However, when applied to systems using chlorine donor(s) which are fed using ORP control, the system experiences undesirable side effects from shock feeding MPS. The addition of MPS increases the ORP of the chlorine donor(s) system. When MPS is added, the ORP of the system rises above that provided by the chlorine donor(s) As long as the ORP value remains above the set point established for the chlorine donor(s) system, no chlorine donor is fed. Since many of the contaminants entering the water do not react directly with MPS without first being oxidized by the chlorine donor(s), these substances further accumulate, thereby compounding the problem.

SUMMARY OF THE INVENTION

This invention incorporates an innovative process that allows the aquatic facility to maintain the desired ORP and oxidize the chlorinated volatile substances in the bulk water, while not exceeding the free chlorine limits established by local health departments.

This process incorporates optimization of the rate of oxidation by controlling the feedrate and ratio of two oxidizers, the primary oxidizer being a halogen donor, e.g. trichloroisocyanuric acid, dichloroisocyanuric acid, sodium bromide, hydantoin based bromines, gaseous chlorine, calcium hypochlorite, sodium hypochlorite, lithium hypochlorite and mixtures thereof; the other being a peroxygen compound selected from hydrogen peroxide, sodium peroxide, sodium perborate, potassium monopersulfate, sodium peroxydisulfate, potassium peroxide, potassium perborate, sodium monopersulfate, potassium peroxydisulfate, ammonium peroxydisulfate, ammonium monopersulfate and mixtures thereof. In a preferred embodiment the peroxygen compound is potassium monopersulfate (MPS). The ratio of MPS to halogen donor, e.g. chlorine donor(s) is optimized to sustain the desired PPM range of chlorine, while achieving an ORP of 780–820 mV. By optimizing and controlling the feedrate and ratios of a halogen donor to maintain the desired ORP, the rate of oxidation is maintained at a level sufficient to prevent the accumulation of undesirable halogenated byproducts. When applied to an aquatic facility, the effects of poor air and water quality can be reduced and even eliminated.

The process optimizes the ORP by incorporating the necessary process control and feed equipment to sustain a set-point thereby controlling the concentration of undesirable by-products in the water.

An objective of the invention is to eliminate volatile halogenated compounds from water and air by maintaining a level of oxidation potential. The feedrate and ratio of halogen donor and peroxygen compound are optimized to sustain the desired PPM range of halogen and sustain an ORP of 780–820 mv. Sustaining these parameters will prevent or even reverse the accumulation of combined halogen and other halogenated volatile compounds which contaminate the air and water of aquatic facilities, in particular indoor aquatic facilities.

Another objective of the invention is to teach a process of operating an aquatic facility under conditions of "Continuous Breakpoint Halogenation and Peroxygenation".

Yet another objective of the invention is to improve the air quality around closed water systems by removal of halogenated compounds through re-absorption followed by oxidation thereof with, e.g. HOCL.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 1:
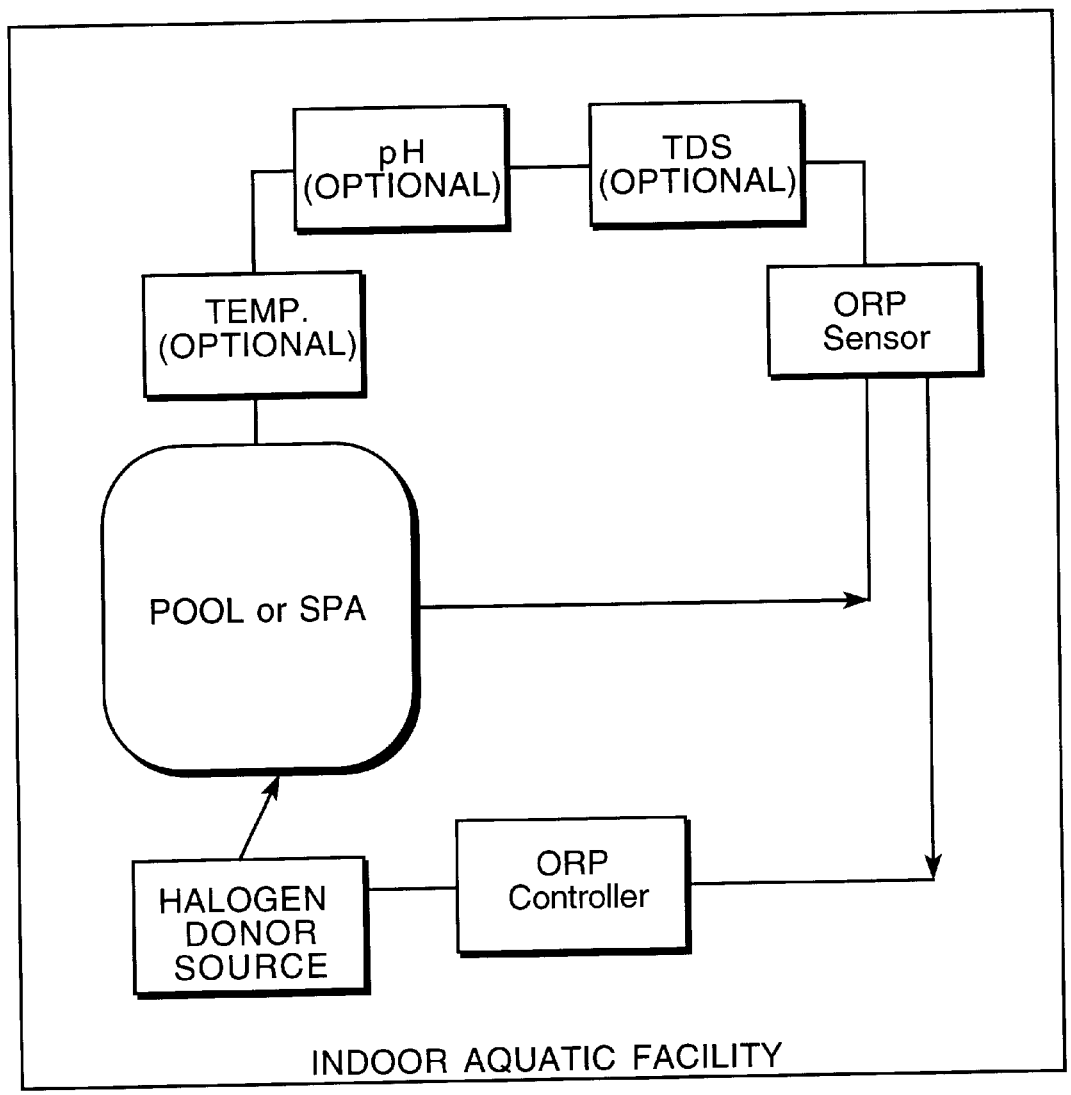
FIG. 1 is a diagrammatic representation of the process of the instant invention.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Referring to FIG. 1, a typical indoor aquatic facility is characterized. Water from the pool or spa flows past an ORP sensor. Optionally, the water may further flow past a sensor which measures total dissolved solids (TDS), temperature and pH. Output from the ORP sensor is transmitted to a controller which calls for the addition of both a halogen donor source and a peroxygen source to the pool water in accordance with selected process parameters.

An innovative process has been developed that allows the aquatic facility to maintain the desired ORP, oxidize the halogenated volatile substances in the bulk water, while not exceeding the free halogen limits established by local health departments.

Oxidation Reduction Potential is a qualitative measurement of the oxidation or reduction power of a solution. ORP controllers have been used in aquatics since 1972 when the Stranco Company developed and introduced these systems to the industry. Despite the use of ORP controllers in tens of thousands of aquatic facilities, the issue of poor air and water quality continues to be the universal and primary problem with indoor aquatic facilities.

While ORP has been established as the primary indicator of determining the inactivation rates of various bacteria and viruses, dosing aquatic water with part per million (PPM) measurement of halogen has been the method used for meeting the oxidation needs of the aquatic facility. For example, while 650 mV is commonly used as the minimum required oxidation potential to ensure sanitized conditions in a pool or spa, the health departments still require PPM levels of halogen, e.g. chlorine.

Despite maintaining health departments levels of halogen and/or operating with ORP levels in excess of 650 mV, following prescribed methods of superchlorination (breakpoint chlorination) as described on the product literature and in the "Certified Pool Operators" (CPO) training course, the problems resulting from incomplete oxidation are widespread.

This process incorporates optimizing the rate of oxidation by controlling the feedrate and ratio of two oxidizers, the primary oxidizer being a halogen donor(s), the other being a peroxygen compound, e.g. Potassium monopersulfate (MPS). The ratio of MPS to halogen donor(s) is optimized to sustain the desired PPM range of halogen, while achieving an ORP of 780–820 mV. By optimizing and controlling the feedrate and ratios of a halogen donor to maintain the desired ORP, the rate of oxidation is sufficient to prevent the accumulation of undesirable chlorinated byproducts. When applied to an aquatic facility, the effects of poor air and water quality can be reduced and even eliminated.

It has been demonstrated that optimizing the ratio of halogen donor(s) to peroxygen compound, while controlling their combined feedrate using ORP, effectively reduces or eliminates the problems resulting from the accumulation of volatile halogenated substances. This is achieved while maintaining lower PPM levels of free halogen than is otherwise required in a strictly halogen donor(s) system.

This process involves: achieving and sustaining an optimum concentration of free halogen, e.g. free chlorine, of between 0.2–10 ppm, addition of peroxygen, e.g. MPS to raise the solution's ORP to 750–850 mV (preferably 760–800 mV), controlling the feed of both oxidizers using an ORP controller, optimizing the ratio of halogen donor(s) to peroxygen compound to sustain the optimized halogen donor(s) while achieving the desired ORP. By sustaining these conditions, the problems created by poor air and/or water quality resulting from the presence of these undesirable byproducts can be reversed.

This invention ensures a sustained high rate of oxidation in the bulk water of the pool, spas, and other aquatic water systems despite the presence of accumulated demand. It has been found that the undesirable byproducts cannot be sustained in an environment possessing this level of oxidation potential. Therefore, by implementing this invention, the aquatic facility will be operating under the conditions of "Continuous Breakpoint Chlorination".

By operating in the conditions described, the byproducts produced during the initial step of oxidation are not allowed to accumulate. The byproducts are an intermediate step in the continuing process of oxidation. While these byproducts are initially produced, they are not allowed to accumulate, and shortly thereafter, are destroyed by the continued oxidation. By preventing the accumulation of these volatile byproducts, their respective partial pressures are minimized, and the problems of poor air quality are minimized or prevented. Also, in aquatic facilities that currently experience these problems, by implementing this application, the problems of poor air quality resulting from these chlorinated compounds can be reversed through re-absorption of the volatile chlorinated compounds, followed by oxidation, even while maintaining substoichiometric levels of free halogen. The re-absorption process follows Henry's Law of Diffusion.

This development is important to the aquatics industry since its implementation means halogen feedrates can be controlled below maximum regulated levels while preventing or even reversing the accumulation of combined halogen and other chlorinated volatile compounds which contaminate the air and water of aquatic facilities, in particular, indoor aquatic facilities.

EXAMPLE 1

Figure 2:
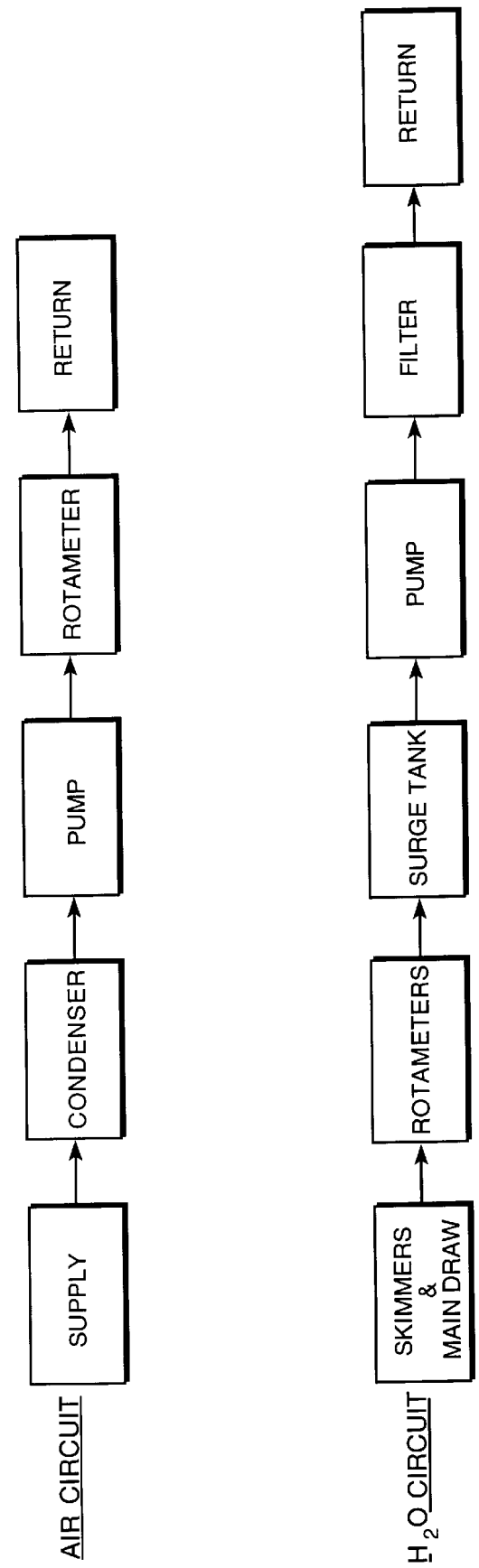
FIG. 2 is a Circuit Diagram of the Air and Water Flow in the test device according to Example 1.

A testing device as shown in FIG. 2 was designed and built to simulate the water and air environment of an indoor aquatic facility. The system was designed to control the following:

$H_2O$ temperature;

Air circulation rates;

Air exchange rates;

Water turnover rates (filtered water);

Water exchange rates.

Instrumentation for automatic monitoring and recording of ORP and pH were incorporated.

A condenser was installed in the air circulation system. The condenser allowed for scheduled sampling of the condensate.

A micro-titration system was incorporated for precise feed of various reagents for adjusting ORP, pH, etc.

The test device was initially prepared for use by the addition of water to 50% of the skimmer line. The tank representing the surge pit was filled to 50%. The tank lid was sealed.

Condensate samples were collected by chilling the air prior to the air circulation pump. Condensate was collected for 20 minutes, the measured sample was tested using standard DPD methods for chlorine that incorporated a HACH DR2000 spectrophotometer.

Laboratory grade ammonium chloride was used as the nitrogen source for the generation of chloramines. A measured amount was added to the water of the test device. The water and air circulation pumps were activated and adjusted to achieve desired circulation and exchange rates.

A measured dosage of chlorine in the form of 5.25% liquid bleach was added to the water to induce the formation of combined chlorine. After providing sufficient contact time, incremental dosages of bleach were added to achieve and sustain the desired ORP of 800 mV. Condensate and water samples were periodically tested for free and total chlorine using standard methods. ORP and pH readings were also recorded.

TABLE 1

| Lapsed Time (minutes) | ppm free (water) | ppm combined (water) | ppm combined (condensate) |
| --- | --- | --- | --- |
| 0 | 0.24 | 1.50 | 0.00 |
| 45 | 4.50 | | 4.35 |
| 90 | 4.46 | | 2.18 |
| 135 | 4.40 | | 1.75 |
| 180 | 4.32 | | 1.45 |
| 225 | 4.26 | | 1.40 |

Results demonstrate that a comparable rate of chloramine destruction can be achieved while sustaining lower concentrations of free available chlorine, at an oxidation potential of approximately 780 mV.

EXAMPLE 2—FIELD TRIAL

An indoor aquatic facility with a 166,500 gallon lap-pool, and a 14,400 gallon splash pool incorporating a water slide had experienced chronic air and water quality problems. Combined chlorine in the water of both pools (water is mixed in the surge tank), was consistently above 1.00 ppm. Odors in the air were strong from chloramines.

The facility had utilized an ORP control system with calcium hypochlorite as the primary sanitizer/oxidizer. Potassium monopersulfate had been fed at 4 times the suggested concentrations as described on the manufacturer's directions. Superchlorination had been incorporated every 3 weeks at a concentration three times that taught by the Certified Operators Training (CPO), and the Aquatic Facilities Operator (AFO) course.

Initially, condensate from the air handling systems dehumidifier was collected and tested using standard methods FAS-DPD test for chlorine.

Day One—3:00 pm . . . 0.6 ppm total chlorine
Day One—7:00 pm . . . 0.8 ppm total chlorine
Day Two—9:00 am . . . 0.8 ppm total chlorine Initially, the system was started using calcium hypochlorite to achieve the targeted ORP of 780 mV. The Free Chlorine levels needed to sustain the ORP at 780 mV generally ranged from 4 to 6 ppm, with one day requiring 18 ppm during a high chlorine demand period.

The two oxidizer approach in accordance with the teachings of the instant invention was then instituted using calcium hypochlorite and potassium monopersulfate. The oxidizers' feed rate was optimized to achieve the desired free chlorine concentration in the water (1.5–2.0 ppm), while sustaining the targeted ORP of 780 mV using monopersulfate.

Within 3 days of implementing the new program, the combined chlorine in the water dropped to undetectable levels using FAS-DPD test for chlorine & Total Oxidant. Free chlorine was consistently between the 1.0–2.0 ppm, and ORP was held at 780 mV±1.0%. The odors and skin and eye irritation problems were eliminated.

To help quantify the reduction in chloramines from the air, condensate samples were later tested following standard DPD methods.

Day One—6:30 am . . . 0.0 ppm (no color change after 2 minutes)
Day One—7:30 pm . . . 0.0 ppm (no color change after 2 minutes)
Day Two—9:00 am . . . 0.0 ppm (no color change after 2 minutes)

Along with the dramatic improvements in air and water quality, chemical use dropped:

| Chemical used | Before (lbs/week) | After (lbs/week) |
| --- | --- | --- |
| Monopersulfate | 74 | 55 |
| Calcium hypochlorite | 80 | 25 |
| Chlorine shock | 69 | 0 |

Although the invention is described in terms of a specific embodiment, it will be readily apparent to those skilled in this art that various modifications, rearrangements and substitutions can be made without departing from the spirit of the invention. The scope of the invention is defined by the claims appended hereto.

What is claimed is:

1. A process for removing volatile halogenated compounds including chloramines and/or bromamines from the air and treating a body of water in an indoor aquatic facility comprising:

disposing an oxidation-reduction potential (ORP) sensor in fluid communication with a body of water within said facility;

continuously monitoring the ORP of said body of water;

comparing the monitored ORP to a set-point value calculated to be within a range effective to permit oxidation of said volatile halogenated compounds, wherein the effective range of ORP is from 750 mv–850 mv;

adding a halogen donor source in an amount and at a rate sufficient to realize an optimum free halogen level sufficient to sanitize said body of water;

adding a peroxygen compound at a rate and in an amount sufficient to maintain the ORP within said effective range;

optimizing the ratio of halogen donor source to peroxygen compound to sustain the optimum free halogen level while maintaining the effective ORP value;

maintaining a sustained high rate of oxidation in said body of water sufficient to cause the volatile halogenated compounds in the air to be reabsorbed therein; and oxidizing the reabsorbed compounds.

2. The process according to claim 1 wherein said halogen donor source is selected from the group consisting of trichloroisocyanuric acid, dichloroisocyanuric acid, sodium bromide, hydantoin based bromines, gaseous chlorine, calcium hypochlorite, sodium hypochlorite, lithium hypochlorite and mixtures thereof.

3. The process according to claim 1 wherein the effective range of ORP is from 760 mv–800 mv.

4. The process according to claim 1 wherein the optimum free halogen level is within a range of 0.2 to 10.0 ppm.

5. The process according to claim 1 wherein the peroxygen compound is selected from the group consisting of hydrogen peroxide, sodium peroxide, sodium perborate, potassium monopersulfate, sodium peroxydisulfate, potassium peroxide, potassium perborate, sodium monopersulfate, potassium peroxydisulfate, ammonium peroxydisulfate and ammonium monopersulfate.

6. The process according to claim 1 further including the step of monitoring and controlling pH.

7. A process for removing dissolved halogenated compounds including chloramines and/or bromamines and preventing their accumulation in circulating water systems comprising:

disposing an oxidation-reduction potential (ORP) sensor in fluid communication with said circulating water system;

continuously monitoring the ORP of said system;

comparing the monitored ORP to a set-point value calculated to be within a range effective to permit oxidation of said halogenated compounds wherein the effective range of ORP is from 750 mv–850 mv;

adding a halogen donor source in an amount and at a rate sufficient to realize an optimum free halogen level sufficient to sanitize said body of water;

adding a peroxygen compound at a rate and in an amount sufficient to maintain the ORP within said effective range;

optimizing the ratio of halogen donor source to peroxygen compound to sustain the optimum free halogen level while maintaining the effective ORP value; and maintaining a sustained high rate of oxidation in said body of water sufficient to destroy any dissolved halogenated compounds within said body of water and prevent further accumulation thereof.

8. The process according to claim 7 wherein said halogen donor source is selected from the group consisting of gaseous chlorine, calcium hypochlorite, sodium hypochlorite, lithium hypochlorite and mixtures thereof.

9. The process according to claim 7 wherein the effective range of ORP is from 760 mv–800 mv.

10. The process according to claim 7 wherein the optimum free halogen level is within a range of 0.2 to 10.0 ppm.

11. The process according to claim 7 wherein the peroxygen compound is selected from the group consisting of hydrogen peroxide, sodium peroxide, sodium perborate, potassium monopersulfate, sodium peroxydisulfate, potassium peroxide, potassium perborate, sodium monopersulfate, potassium peroxydisulfate, ammonium peroxydisulfate and ammonium monopersulfate.

12. The process according to claim 7 further including the step of monitoring and controlling pH.

* * * * *